United States Patent [19]

Gaines et al.

[11] 3,960,457
[45] June 1, 1976

[54] WEAR INDICATOR FOR BALL JOINTS

[75] Inventors: Donald R. Gaines, Farmington; Bronko F. Jelenic, Ann Arbor, all of Mich.

[73] Assignee: Gulf & Western Manufacturing Company (Michigan), Southfield, Mich.

[22] Filed: Dec. 20, 1974

[21] Appl. No.: 535,015

[52] U.S. Cl. .............................. 403/27; 116/114 Q
[51] Int. Cl.² ................... G01D 11/02; F16C 11/06
[58] Field of Search ..... 116/114 Q, 114 AE, 124 D, 116/124 E, DIG. 34; 308/7, 72; 403/27, 131

[56] References Cited
UNITED STATES PATENTS

| | | | |
|---|---|---|---|
| 3,350,121 | 10/1967 | Townsend | 403/131 |
| 3,391,955 | 7/1968 | Gottschald | 403/131 |
| 3,451,701 | 6/1969 | Smith | 308/72 X |
| 3,791,748 | 2/1974 | Goodrich, Jr. et al. | 116/114 Q X |
| 3,813,178 | 5/1974 | Herbenar et al. | 403/27 |
| 3,850,443 | 11/1974 | Hassan | 403/27 X |

*Primary Examiner*—Richard C. Queisser
*Assistant Examiner*—Daniel M. Yasich
*Attorney, Agent, or Firm*—Barnes, Kisselle, Raisch & Choate

[57] ABSTRACT

A ball joint wear detector having an indicator cap carried by a cover underlying a ball of a ball stud member received in a housing member. The indicator cap has a fixed reference surface on an outer ring thereof and a movable indicator surface on a center cup in which an actuator is received which is yieldably urged into engagement with a polar portion of the ball by a membrane of resilient material interconnecting the cup and the outer ring of the indicator cap. When the ball joint is in use, the extent of the axial displacement of the ball relative to the housing due to in-service wear of the ball joint is indicated by the displacement of the indicator surface relative to the fixed surface of the indicator cap which may be visually observed from the exterior of the ball joint.

11 Claims, 6 Drawing Figures

U.S. Patent   June 1, 1976   3,960,457
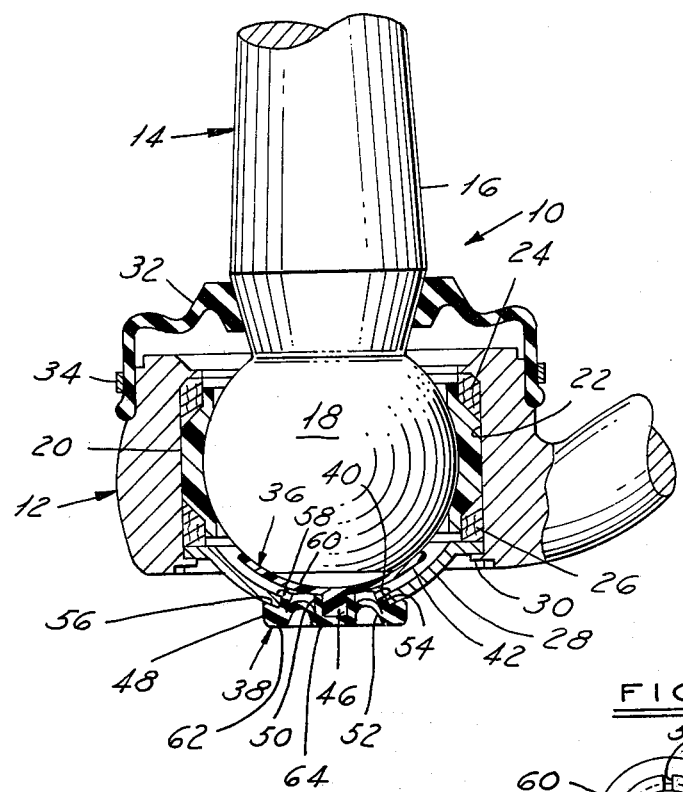
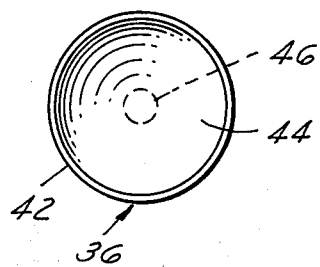
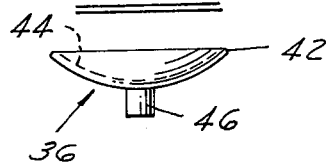
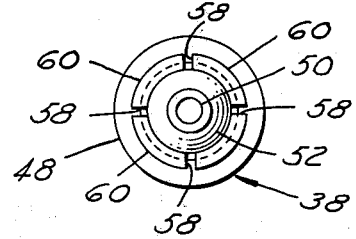
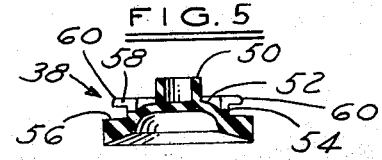
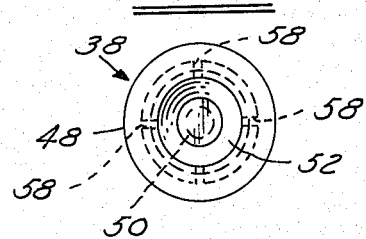

WEAR INDICATOR FOR BALL JOINTS

This invention relates to ball joints and more particularly to wear indicators for ball joints.

Conventional ball joints used in vehicles, such as automobiles, trucks, and off-the-road equipment, become worn in service so that the ball stud member may be shifted generally axially with respect to the housing of the ball joint assembly. This in-service wear of such ball joints is usually detected by manually manipulating the ball joint assembly to feel any play or looseness between the ball and the housing. This method of detecting in-service wear of ball joints is inaccurate, subjective, and difficult to perform if the ball joint is in an inaccessible location or of a large size, such as the ball joints used in heavy-duty, off-the-road equipment. Consequently, this method is unreliable for determining when ball joints worn by in-service use should be replaced.

Objects of this invention are to provide an in-service wear indicator for ball joints which is accurate, responsive to small amounts of wear, reliable, durable, economical to manufacture and assemble, service and maintenance free, and provides a simple, reliable, and objective way of determining in the field when ball joints should be replaced.

These and other objects, features and advantages of this invention will be apparent from the following description, appended claims and accompanying drawing in which:

FIG. 1 is a fragmentary sectional view of a ball joint embodying the in-service wear indicator of this invention.

FIGS. 2 and 3 are top and side views respectively of an actuator of the wear indicator of FIG. 1.

FIGS. 4, 5 and 6 are top, full sectional and bottom views respectively of an indicator cap of the wear indicator of FIG. 1.

Referring in more detail to the drawing, FIG. 1 illustrates a permanently lubricated ball joint 10 embodying this invention with a housing member 12 and a ball stud member 14 pivotally mounted therein. Ball stud member 14 has a stud 16 with an integral ball 18 adjacent one end thereof which is mounted by a retainer ring 18 of a plastic material, such as acetal, in a generally cylindrical cavity 22 extending generally axially through housing 12. Rings 24 and 26 of a fiberous material impregnated with a lubricant are received in cavity 22 adjacent the opposed edges of retainer ring 20, and an end cover 28 underlying a polar portion of ball 18 is retained in cavity 22 adjacent the lower end thereof by a plurality of stakes 30. A dust seal 32 of an elastic material such as rubber, engages stud 16 and is retained on housing member 12 by a retainer band 34 to prevent moisture, dust and other contaminants from entering the housing member.

In accordance with this invention, an actuator 36 is yieldably biased generally axially into engagement with a polar region of ball 18 by an indicator cap 38 received in an aperture 40 through end cover 28. As shown in FIGS. 2 and 3, actuator 36 has a bowl 42 with a spherical surface 44 having a radius of curvature equal to that of ball 18 for mating engagement therewith and an integral axially extending plunger 46. Actuator 36 is made of a low friction, highly wear resistant material, such as polyethylene and acetal plastics.

As shown in FIGS. 4 through 6, indicator cap 38 has a one-piece body with a homogeneously integral outer ring 48, center cup 50, and interconnecting resilient membrane 52 and is made of a resilient elastic material, such as nylon. Outer ring 48 has a circumferentially continuous groove 54 therein which opens radially outwardly and forms a circumferentially continuous sealing surface 56 in ring 48 and a radially extending flange which has four circumferentially spaced slots 58 therethrough providing four retaining fingers 60.

In assembling ball joint 10, retainer ring 20 is slipped over the equatorial portion of ball 18 of ball stud member 14 and the subassembly of the retainer, ball stud member, and seals 24 and 26 is inserted generally axially into cavity 22 of housing member 12. The indicator cap 38 is inserted into hole 40 in end cover 28 so that a portion of the end cover adjacent the hole is received in groove 54 of the indicator cap. Insertion of indicator cap 38 into hole 40 flexes fingers 60 generally radially inward and when they pass through the hole they snap outwardly into engagement with end cover 28 to both firmly retain the indicator cap on the cover and urge sealing surface 56 of the indicator cap into firm sealing engagement with the cover to prevent contaminants from passing into housing member 12 between the indicator cap and the cover. The plunger 46 of actuator 36 is inserted into cup 50 of indicator cap 38, and the end cover 28 with the indicator cap and actuator subassembled thereon is inserted into cavity 22 of housing member 12 and secured therein by stakes 30. As end cover 28 is inserted in the cavity 22, actuator 36 bears on a polar region of ball 18 and displaces cup 50 of the indicator cap 38 relative to the outer ring 48 thereof which flexes membrane 52 thereof to yieldably urge actuator 36 into engagement with ball 18, as may be seen by comparing the sectional views of the indicator cap of FIGS. 5 and 1.

After indicator cap 38, actuator 36, and cover 28 are completely assembled in ball joint 10, the lower exterior face of the indicator cap is machined, such as by milling or grinding, to provide a reference surface 62 on outer ring 48 and an indicator surface 64 on center cup 50 (FIG. 1) which lie in the same plane. Hence, any in-service wear of the ball joint 10 which allows ball 18 to shift generally axially with respect to housing member 12 will be indicated by the generally axial displacement of indicator surface 64 relative to reference surface 62 of the indicator cap 38. Since resilient membrane 52 yieldably biases cup 50 into engagement with actuator 36 and the actuator into engagement with ball 18, indicator surface 64 will be displaced relative to reference surface 62 in proportion to the generally axial displacement of ball 18 and housing 12 relative to each other. Thus, when ball joint 10 is used in the field, the extent of the inservice wear thereof will be indicated by the extent of the displacement of indicator surface 64 relative to reference surface 62 of the indicator cap. This displacement may be detected by either visual observation of the indicator cap or by wiping a finger over the surfaces of the indicator cap from the exterior of the ball joint.

The indicator cap with an indicator displaceable relative to a fixed reference provides a ball joint wear indicator embodying this invention which is accurate, reliable, sensitive, responsive to small amounts of in-service wear and readily observable from the exterior of the ball joint. Ball joint wear detectors embodying this invention have only a few component parts which may be readily molded of suitable plastic material and, hence, are durable, of economical manufacture and assembly and service and maintenance free. The snap-in retention of the indicator cap in the end cover with the actuator received in the cup of the indicator cap provides a device which may be readily and economically assembled. By forming the indicator and reference surfaces on the indicator cap after the indicator cap and its associated plunger have been fully assembled on the ball joint, the need for close manufacturing tolerances of the component parts thereof is eliminated and the normal manufacturing variations of all of the component parts of both the ball joint and the wear indicator and the stack up of manufacturing tolerances is economically corrected or compensated for.

We claim:

1. A ball joint wear indicator comprising, a housing member having a cavity extending generally axially therethrough, a ball stud member having a stud with an integral ball thereon mounted in said cavity of said housing member with said stud projecting generally axially beyond said cavity to the exterior of said housing member for movement of said ball stud member with respect to said housing member, an end cover adjacent the other end of said cavity and also adjacent a generally polar region of said ball and being fixedly carried by said housing member, an actuator bearing on the generally polar region of said ball adjacent said cover, and a one-piece indicator body having a first portion fixedly carried by said cover, a second portion operably connected with said actuator, and a membrane portion homogeneously integral with said first and second portions and yieldably biasing said actuator into engagement with said ball, a reference surface on said first portion of said indicator body, said reference surface being accessible from the exterior of and in fixed relation to said housing member, an indicator surface on said second portion of said one-piece indicator body, said indicator surface being accessible from the exterior of said housing member and operably associated with said actuator for generally axial movement relative to said reference surface in response to generally axial movement of said ball relative to said housing member, and said indicator and reference surfaces of said one-piece body being constructed and arranged to lie in the same plane prior to any in-service wear of the ball joint such that thereafter the extent of any displacement of said reference and indicator surfaces relative to each other provides an indication of the extent of in-service wear of the ball joint.

2. The wear indicator of claim 1 wherein said indicator body is carried by said cover such that said indicator body communicates with both said cavity in said housing member and the exterior of said housing member, and also comprises sealing means providing a seal between said one-piece indicator body and said cover.

3. The wear indicator of claim 1 wherein said cover has an aperture therethrough in which said first portion of said one-piece indicator body is received, and said first portion of said body has a circumferentially continuous groove therein opening generally radially outward to receive therein a portion of said cover adjacent said aperture to mount said one-piece indicator body on said cover.

4. The wear indicator of claim 3 wherein said first portion of said indicator body has a circumferentially continuous sealing portion adjacent said groove which engages said cover to provide a seal between said cover and said indicator body.

5. The wear indicator of claim 4 wherein said first portion of said one-piece body has a plurality of generally radially extending circumferentially spaced fingers adjacent said groove which engage said cover to releasably retain said indicator body in said aperture through said cover.

6. A wear indicator for a ball joint having a housing member with a cavity therein and a ball stud member having a stud and a ball adjacent one end thereof with said ball being mounted in said cavity of said housing member with said stud projecting generally axially beyond said cavity to the exterior of said housing member for relative movement of said members, said wear indicator comprising; a one-piece indicator body of an elastic material having an indicator portion adjacent a generally polar region of said ball, an annular portion of said one-piece indicator body encircling and spaced from said indicator portion and adapted to be fixedly carried by said housing member, and a membrane portion of said one-piece indicator body interposed between and homogeneously integral with said indicator and annular portions, said indicator portion having an indicator surface thereon accessible from the exterior of the ball joint, said annular portion having a reference surface thereon accessible from the exterior of the ball joint, and said membrane portion being constructed and arranged to yieldably bias said indicator portion into operative relationship with said ball such that said indicator surface of said indicator portion is displaced in unison with said ball generally axially with respect to said reference surface of said annular portion in response to generally axial displacement of said ball with respect to said housing member, whereby after said wear indicator is assembled on a ball joint any generally axial displacement of said reference and indicator surface relative to each other provides an indication of the extent of in-service wear of the ball joint.

7. The wear indicator of claim 6 which also comprises a separate actuator member which in assembly is interposed between and bears on said indicator portion and the ball of the ball joint.

8. The wear indicator of claim 6 wherein said indicator and reference surfaces of said one-piece body lie in the same plane prior to any in-service wear of the ball joint such that thereafter the extent of any displacement of said reference and indicator surfaces relative to each other provides an indication of the extent of in-service wear of the ball joint.

9. The wear indicator of claim 6 wherein after said one-piece indicator body is mounted on the ball joint such that it is fixedly carried by the housing member, sufficient material is removed from at least one of said indicator and reference surfaces of said one-piece body such that they lie in the same plane prior to any in-service wear of the ball joint so that thereafter the extent of any displacement of said reference and indicator surfaces relative to each other provides an indication of the extent of in-service wear of the ball joint.

10. The wear indicator of claim 6 wherein said one-piece body is adapted to be received in an aperture through an end cover carried by the housing member and said annular ring has a circumferentially continuous groove therein opening generally radially outwardly thereof to receive therein a portion of the end cover adjacent the aperture therethrough thereby mounting said one-piece body on the end cover and, providing a seal between said one-piece body and the end cover.

11. The wear indicator of claim 10 wherein said annular portion of said one-piece body has a plurality of generally radially extending circumferentially spaced fingers adjacent said groove which are adapted to engage the end cover to releasably retain said indicator body in the aperture through the end cover.

* * * * *

UNITED STATES PATENT OFFICE
CERTIFICATE OF CORRECTION

Patent No. 3,960,457  Dated June 1, 1976

Inventor(s) Donald R. Gaines et al

It is certified that error appears in the above-identified patent and that said Letters Patent are hereby corrected as shown below:

On the Cover Sheet cancel the Drawing Figure and substitute the attached Figure.

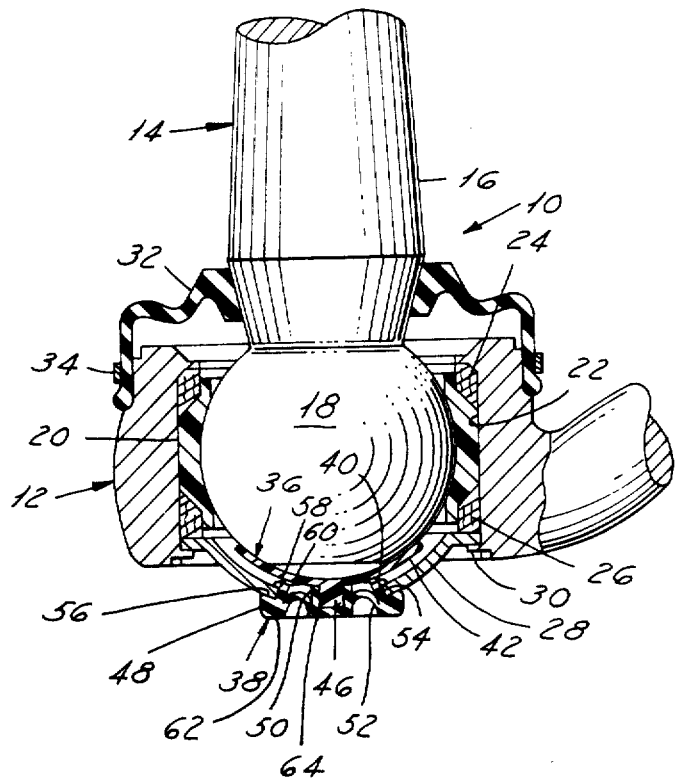

Signed and Sealed this

Fourteenth Day of September 1976

[SEAL]

Attest:

RUTH C. MASON
*Attesting Officer*

C. MARSHALL DANN
*Commissioner of Patents and Trademarks*